United States Patent
McConville et al.

(10) Patent No.: US 6,271,325 B1
(45) Date of Patent: Aug. 7, 2001

(54) METHOD OF POLYMERIZATION

(75) Inventors: David H. McConville, Houston, TX (US); Richard R. Schrock, Winchester, MA (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/312,878

(22) Filed: May 17, 1999

(51) Int. Cl.[7] ........................................................ C08F 2/00
(52) U.S. Cl. .................. 526/217; 526/72; 526/90; 526/107; 526/126; 526/903; 502/167; 502/232; 502/227
(58) Field of Search .................. 526/107, 72, 90, 526/126, 903, 217; 502/167, 232, 227

(56) References Cited

U.S. PATENT DOCUMENTS

| | | | |
|---|---|---|---|
| 4,057,565 | 11/1977 | Manzer | 260/429 |
| 4,225,464 | * 9/1980 | Schollten et al. | 252/458 |
| 5,372,882 | * 12/1994 | Peiffer et al. | 428/34.9 |
| 5,426,243 | 6/1995 | Lecouve | 568/737 |
| 5,527,930 | * 6/1996 | Sangokoya | 556/179 |
| 5,637,660 | 6/1997 | Nagy et al. | 526/160 |
| 5,707,913 | 1/1998 | Schlund et al. | 502/102 |
| 5,726,115 | 3/1998 | Horton et al. | 502/152 |
| 5,798,427 | 8/1998 | Foster et al. | 526/352 |
| 5,889,128 | * 3/1999 | Schrock et al. | 526/107 |

FOREIGN PATENT DOCUMENTS

| | | |
|---|---|---|
| 0197310 A2 | | |
| A3 | 10/1986 | (EP) . |
| 0241560 A1 | 10/1987 | (EP) . |
| 0751142 A2 | 1/1997 | (EP) . |
| 0816372 A2 | 1/1998 | (EP) . |
| 0816384 A2 | | |
| A3 | 1/1998 | (EP) . |
| 0 893 454 | * 8/1998 | (EP) . |
| 0803520 B1 | 12/1998 | (EP) . |
| 0890575 A1 | 1/1999 | (EP) . |
| 0893454 A1 | 1/1999 | (EP) . |
| 02-78663 | 3/1990 | (JP) . |
| 08-081415 | 7/1996 | (JP) . |
| 08-277307 | 10/1996 | (JP) . |
| 10-7712 | 1/1998 | (JP) . |
| 10-45904 | 2/1998 | (JP) . |
| WO 91/12285 | 8/1991 | (WO) . |
| WO 92/12162 | 7/1992 | (WO) . |
| WO 94/21700 | 9/1994 | (WO) . |

(List continued on next page.)

OTHER PUBLICATIONS

Horton et al., *Organometallics*, 15, 2672–2674, 1996.*
Guerin et al., *Organometallics*, 17, 5172–5177, 1998.*
*Organometallics*, Bei et al., vol. 16, pp. 3282–3302 (1997).
*Organometallics*, Grubbs, vol. 17, pp. 3149–3151 (1998).
*Macromolecules*, Repo, vol. 30, pp. 171–175 (1997).

*Polyhedron*, Guerin et al., vol. 17 (5–6), pp. 917–923 (1998).
*Inorganic Chemistry*, Furhman/Kempe et al., vol. 35, pp. 6742–6745 (1996).
*Organometallics*, Guerin et al., vol. 15 (26), pp. 5586–5590 (1996).
*Organometallics*, Guerin et al., vol. 17 (23), pp. 5172–5177 (1998).
*Macromolecular Chemistry and Physics*, Silvestro et al., vol. 197, No. 10, pp. 3209–3228 (1996).
*Journal of Organometallic Chemistry*, Harkonen et al., vol. 519, No. 1, pp. 205–208 (1996).
*J. Chem. Soc. Dalton Trans.*, Cloke et al., pp. 25–30 (1995).
*Journal of Organometallic Chemistry*, Clark et al., vol. 501, pp. 333–340 (1995).
*J. Am. Chem. Soc.*, Baumann et al., vol. 119, pp. 3830–3831 (1997).

(List continued on next page.)

Primary Examiner—David W. Wu
Assistant Examiner—Ling-Siu Choi

(57) ABSTRACT

This invention relates to a composition of matter represented by the formula below, and to a polymerization process comprising combining an olefin in the gas or slurry phase with an activator, a support and a compound represented by the following formula:

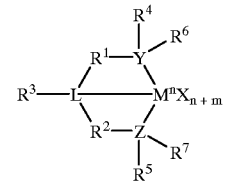

wherein
M is a group 3 to 14 metal,
each X is independently an anionic leaving group,
n is the oxidation state of M,
m is the formal charge of the YZL ligand,
Y is a group 15 element,
Z is a group 15 element,
L is a group 15 or 16 element,
$R^1$ and $R^2$ are independently a $C_1$ to $C_{20}$ hydrocarbon group, a heteroatom containing group, silicon, germanium, tin, lead, phosphorus, a halogen,
$R^1$ and $R^2$ may also be interconnected to each other,
$R^3$ is absent, or is hydrogen, a group 14 atom containing group, a halogen, a heteroatom containing group,
$R^4$ and $R^5$ are independently an aryl group, a substituted aryl group, a cyclic alkyl group, a substituted cyclic alkyl group, or multiple ring system,
$R^6$ and $R^7$ are independently absent or hydrogen, halogen, a heteroatom or a hydrocarbyl group, or a heteroatom containing group.

38 Claims, No Drawings

FOREIGN PATENT DOCUMENTS

WO 96/08498    3/1996   (WO).
WO 97/42197 *  11/1997  (WO).
WO 97/45434    12/1997  (WO).
WO 97/48735    12/1997  (WO).
WO 97/48736    12/1997  (WO).
WO 98/27124    6/1998   (WO).
WO 98/30569    7/1998   (WO).
WO 98/30612    7/1998   (WO).
WO 98/34964    8/1998   (WO).
WO 98/37109    8/1998   (WO).
WO 98/46651    10/1998  (WO).
WO 98/55467    12/1998  (WO).
WO 99/02472    1/1999   (WO).
WO 99/02536    1/1999   (WO).
WO 99/12981    3/1999   (WO).

OTHER PUBLICATIONS

*J. Am. Chem. Soc.*, Scollard et al., vol. 118, pp. 10008–10009 (1996).

*Organometallics*, Horton et al., vol. 15, pp. 2672–2674 (1996).

*Organometallics*, Guerin et al., vol. 15, pp. 5085–5089 (1996).

* cited by examiner

METHOD OF POLYMERIZATION

FIELD OF THE INVENTION

This invention relates to olefin polymerization catalysts containing a metal atom bound to at least two group 15 atoms and their use in gas or slurry phase to produce polyolefins.

BACKGROUND OF THE INVENTION

The intense commercialization of metallocene polyolefin catalysts (metallocene being cyclopentadienyl based transition metal catalyst compounds) has led to widespread interest in the design of non-metallocene, homogeneous catalysts, particularly for use in the economical gas and slurry phase processes. This field is more than an academic curiosity as new, non-metallocene catalysts in gas or slurry phase may provide an easier, more economical pathway to currently available products and may also provide product and process opportunities which are beyond the capability of metallocene catalysts in the gas or slurry phase.

Anionic, multidentate heteroatom ligands have received the most attention in non-metallocene polyolefins catalysis. Notable classes of bidentate anionic ligands which form active polymerization catalysts include N—N⁻ and N—O⁻ ligand sets. Examples of these types of non-metallocene catalysts include amidopyridines (Kempe, R., "Aminopyridinato Ligands—New Directions and Limitations", 80$^{th}$ Canadian Society for Chemistry Meeting, Windsor, Ontario, Canada, Jun. 1–4, 1997. Kempe, R. et al, *Inorg. Chem.* 1996 vol 35 6742.) Likewise, recent reports by Jordan et al. of polyolefin catalysts based on hydroxyquinolines (Bei, X.; Swenson, D. C.; Jordan, R. F., *Organometallics* 1997, 16, 3282) have been interesting even though the catalytic activities of Jordan's hydroxyquinoline catalysts are low.

Schrock et al in U.S. Pat. No. 5,889,128 discloses a process for the living polymerization of olefins in solution using initiators having a metal atom and a ligand having two group 15 atoms and a group 16 atom or three group 15 atoms. In particular, the solution phase polymerization of ethylene using {[NON]ZrMe}[MeB(C$_6$F$_5$)$_3$] or {[NON] ZrMe(PhNMe$_2$)]}[B(C$_6$F$_5$)$_4$] is disclosed in examples 9 and 10.

EP 893 454 A1 discloses unsupported transition metal amide compounds used in combination with activators to polymerize olefins in the solution phase.

Ethylenebis(salicylideneiminato)zirconium dichloride combined with methyl alumoxane deposited on a support and unsupported versions were used to polymerize ethylene by Repo et al in Macromolecules 1997, 30, 171–175.

Thus there is a need in the art for gas or slurry phase processes to produce polyolefins using new and different supported catalyst systems.

SUMMARY OF THE INVENTION

This invention relates to a catalytic molecule, and a catalyst system comprising a support, an activator, and a metal catalyst compound.

In one aspect, the invention relates to a catalyst system comprising a support, an activator and a metal catalyst compound comprising a group 3 to 14 metal atom bound to at least one anionic leaving group and also bound to at least two group 15 atoms, at least one of which is also bound to a group 15 or 16 atom through another group which may be a $C_1$ to $C_{20}$ hydrocarbon group, a heteroatom containing group, silicon, germanium, tin, lead, phosphorus, or a halogen, wherein the group 15 or 16 atom may also be bound to nothing or a hydrogen, a group 14 atom containing group, a halogen, or a heteroatom containing group, and wherein each of the two group 15 atoms are also bound to a cyclic group and may optionally be bound to hydrogen, a halogen, a heteroatom or a hydrocarbyl group, or a heteroatom containing group.

This invention relates to the gas or slurry phase polymerization of olefins using an olefin polymerization catalyst system comprising an activator, a support and a transition metal compound represented by the formula:

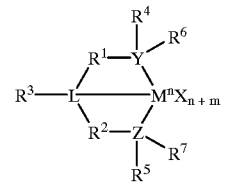

wherein
M is a group 3 to 12 transition metal or a group 13 or 14 main group metal, each X is independently an anionic leaving group,
n is the oxidation state of M,
m is the formal charge of the YZL ligand,
Y is a group 15 element,
Z is a group 15 element,
L is a group 15 or 16 element,
$R^1$ and $R^2$ are independently a $C_1$ to $C_{20}$ hydrocarbon group, a heteroatom containing group, silicon, germanium, tin, lead, phosphorus, halogen,
$R^1$ and $R^2$ may also be interconnected to each other,
$R^3$ is absent, or is hydrogen, a group 14 atom containing group, a halogen, a heteroatom containing group,
$R^4$ and $R^5$ are independently an aryl group, a substituted aryl group, a cyclic alkyl group, a substituted cyclic alkyl group, or multiple ring system, and
$R^6$ and $R^7$ are independently absent or hydrogen, halogen, heteroatom or a hydrocarbyl group, or a heteroatom containing group.

By "formal charge of the YZL ligand" is meant the charge of the entire ligand absent the metal and the leaving groups X.

By "$R^1$ and $R^2$ may also be interconnected to each other" is meant that $R^1$ and $R^2$ may be directly bound to each other or may be bound to each other through other groups.

The activator is preferably an aluminum alkyl, an alumoxane, a modified alumoxane, a non-coordinating anion, a borane, a borate or a combination thereof.

In another aspect, the invention relates to a catalytic molecule comprising the transition metal compound represented by the formula set forth above.

DETAILED DESCRIPTION OF THE INVENTION

The present invention relates to a catalytic molecule (metal catalyst), and a catalyst system comprising a support, an activator, and the metal catalyst. The metal catalyst shows surprising ability to be immobilized on a support, activated by an activator, and surprising robustness and catalytic activity when supported and activated. The catalyst molecule itself is described, hereinafter, with reference to its combination with an activator.

In a preferred embodiment the activator is combined with a compound represented by the formula:

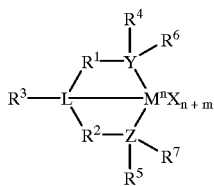

wherein

M is a group 3–12 transition metal or a group 13 or 14 main group metal, preferably a group 4, 5, or 6 metal, preferably zirconium or hafnium, each X is independently an anionic leaving group, preferably hydrogen, a hydrocarbyl group, a heteroatom or a halogen, n is the oxidation state of M, preferably +3, +4, or +5, preferably +4, m is the formal charge of the YZL ligand, preferably 0, −1, −2 or −3, preferably −2, L is a group 15 or 16 element, preferably nitrogen, Y is a group 15 element, preferably nitrogen or phosphorus, Z is a group 15 element, preferably nitrogen or phosphorus, $R^1$ and $R^2$ are independently a $C_1$ to $C_{20}$ hydrocarbon group, a heteroatom containing group having up to twenty carbon atoms, silicon, germanium, tin, lead, phosphorus, a halogen, preferably a $C_2$ to $C_6$ hydrocarbon group, preferably a $C_2$ to $C_{20}$ alkyl, aryl or aralkyl group, preferably a linear, branched or cyclic $C_2$ to $C_{20}$ alkyl group, $R^1$ and $R^2$ may also be interconnected to each other, $R^3$ is absent or a hydrocarbon group, hydrogen, a halogen, a heteroatom containing group, preferably a linear, cyclic or branched alkyl group having 1 to 20 carbon atoms, more preferably $R^3$ is absent or hydrogen, $R^4$ and $R^5$ are independently an aryl group, a substituted aryl group, a cyclic alkyl group, a substituted cyclic alkyl group, a cyclic aralkyl group, a substituted cyclic aralkyl group or multiple ring system, preferably having up to 20 carbon atoms, preferably between 3 and 10 carbon atoms, preferably a $C_1$ to $C_{20}$ hydrocarbon group, a $C_1$ to $C_{20}$ aryl group or a $C_1$ to $C_{20}$ aralkyl group, and $R^6$ and $R^7$ are independently absent, or hydrogen, halogen, heteroatom or a hydrocarbyl group, preferably a linear, cyclic or branched alkyl group having 1 to 20 carbon atoms, more preferably absent.

An aralkyl group is defined to be a substituted aryl group.

In a preferred embodiment, L is bound to one of Y or Z and one of $R^1$ or $R^2$ is bound to L and not to Y or Z.

In an alternate embodiment $R^3$ and L do not form a heterocyclic ring.

In a preferred embodiment $R^4$ and $R^5$ are independently a group represented by the following formula:

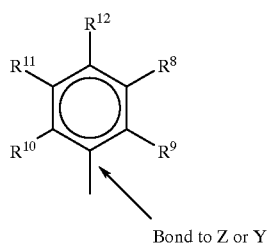

wherein $R^8$ to $R^{12}$ are each independently hydrogen, a $C_1$ to $C_{40}$ alkyl group, a heteroatom, a heteroatom containing group containing up to 40 carbon atoms, preferably a Cl to $C_{20}$ linear or branched alkyl group, preferably a methyl, ethyl, propyl or butyl group, any two R groups may form a cyclic group and/or a heterocyclic group. The cyclic groups may be aromatic. In a preferred embodiment $R^9$, $R^{10}$ and $R^{12}$ are independently a methyl, ethyl, propyl or butyl group, in a preferred embodiment $R^9$, $R^{10}$ and $R^{12}$ are methyl groups, and $R^8$ and $R^{11}$ are hydrogen.

In a particularly preferred embodiment $R^4$ and $R^5$ are both a group represented by the following formula:

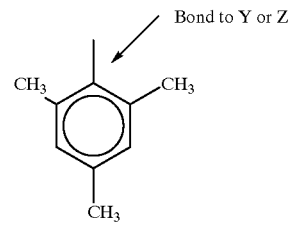

In this embodiment, M is preferably zirconium or hafnium, most preferably zirconium; each of L, Y, and Z is nitrogen; each of $R^1$ and $R^2$ is —$CH_2$—$CH_2$—; $R^3$ is hydrogen; and $R^6$ and $R^7$ are absent.

These metal compounds are prepared by methods known in the art, such as those disclosed in U.S. Pat. No. 5,889,128 and the references cited therein which are all incorporated by reference herein. A preferred direct synthesis of these compounds comprises reacting the neutral ligand with $M^nX_n$ (M is a group 3–14 metal, n is the oxidation state of M, X is an anionic group, such as halide, in a non-coordinating or weakly coordinating solvent, such as ether, toluene, xylene, benzene, methylene chloride, and/or hexane or other solvent having a boiling point above 60° C., at about 20 to about 150° C. (preferably 20 to 100° C.), preferably for 24 hours or more, then treating the mixture with an excess (such as four equivalents) of an alkylating agent, such as methyl magnesium bromide in ether. The magnesium salts are removed by filtration, and the metal complex isolated by standard techniques.

In a preferred embodiment this invention relates to a method to prepare a metal compound comprising reacting a neutral ligand with a compound represented by the formula $M^nX_n$ (where M is a group 3–14 metal, n is the oxidation state of M, X is an anionic leaving group) in a non-coordinating or weakly coordinating solvent, at about 20° C. or above, preferably at about 20 to about 100° C., then treating the mixture with an excess of an alkylating agent, then recovering the metal complex. In a preferred embodiment the solvent has a boiling point above 60° C., such as ether, toluene, xylene, benzene, methylene chloride and/or hexane.

This invention further relates to a method to prepare a metal adduct comprising reacting a neutral ligand with a compound represented by the formula $M^nX_n$ (where M is Zr or Hf, n is the oxidation state of M, X is a halogen) in a non-coordinating or weakly coordinating solvent, at 20° C. or more, preferably at about 20 to about 100° C. then recovering the metal adduct.

This invention further relates to the reaction product of a neutral ligand reacted with a compound represented by the formula $M^nX_n$ (where M is Zr or Hf, n is the oxidation state of M, X is an anionic leaving group), in a non-coordinating or weakly coordinating solvent at about 20° C. or above, preferably at about 20 to about 100° C.

In a preferred embodiment the neutral ligand is represented by the formula:

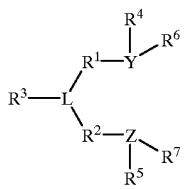

Y is a group 15 element, preferably nitrogen or phorphorus,
Z is a group 15 element, preferably nitrogen or phorphorus,
L is a group 15 or 16 element, preferably nitrogen,
$R^1$ and $R^2$ are independently a $C_1$ to $C_{20}$ hydrocarbon group, a heteroatom containing group, silicon, germanium, tin, lead, phosphorus, a halogen,
$R^1$ and $R^2$ may also be interconnected to each other,
$R^3$ is absent, or is hydrogen, a group 14 atom containing group, a halogen, a heteroatom containing group,
$R^4$ and $R^5$ are independently an aryl group, a substituted aryl group, a cyclic alkyl group, a substituted cyclic alkyl group, or multiple ring system,
$R^6$ and $R^7$ are independently absent or hydrogen, halogen, a heteroatom or a hydrocarbyl group, or a heteroatom containing group.

The transition metal compounds described herein are preferably combined with one or more activators to form an olefin polymerization catalyst system. Preferred activators include alkyl aluminum compounds (such as diethylaluminum chloride), alumoxanes, modified alumoxanes, non-coordinating anions, non-coordinating group 13 metal or metalliod anions, boranes, borates and the like. It is within the scope of this invention to use alumoxane or modified alumoxane as an activator, and/or to also use ionizing activators, neutral or ionic, such as tri (n-butyl) ammonium tetrakis (pentafluorophenyl) boron or a trisperfluorophenyl boron metalloid precursor which ionize the neutral metallocene compound. Other useful compounds include triphenyl boron, triethyl boron, tri-n-butyl ammonium tetraethylborate, triaryl borane and the like. Other useful compounds include aluminate salts as well.

There are a variety of methods for preparing alumoxane and modified alumoxanes, non-limiting examples of which are described in U.S. Pat. Nos. 4,665,208, 4,952,540, 5,091, 352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253 and 5,731,451 and European publications EP-A-0 561 476, EP-B1 -0 279 586 and EP-A-0 594-218, and PCT publication WO 94/10180, all of which are herein fully incorporated by reference.

Ionizing compounds may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-A-0 426 637, EP-A-500 944, EP-A-0 277 003 and EP-A-0 277 004, and U.S. Pat. Nos. 5,153,157, 5,198,401, 5,066,741, 5,206,197, 5,241,025, 5,387,568, 5,384,299 and 5,502,124 and U.S. patent application Ser. No. 08/285,380, filed Aug. 3, 1994, all of which are herein fully incorporated by reference. Other activators include those described in PCT publication WO 98/07515 such as tris (2,2',2"- nonafluorobiphenyl) fluoroaluminate, which is fully incorporated herein by reference. Combinations of activators are also contemplated by the invention, for example, alumoxanes and ionizing activators in combinations, see for example, PCT publications WO 94/07928 and WO 95/14044 and U.S. Pat. Nos. 5,153,157 and 5,453,410 all of which are herein fully incorporated by reference. Also, methods of activation such as using radiation and the like are also contemplated as activators for the purposes of this invention.

In general the transition metal compound and the activator are combined in ratios of about 1000:1 to about 0.5:1. In a preferred embodiment the transition metal compound and the activator are combined in a ratio of about 300:1 to about 1: 1, preferably about 10:1 to about 1: 1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

Polymerization Process of the Invention:

The catalysts and catalyst systems described above are suitable for use in the polymerization process of the invention. The polymerization process of the invention includes a solution, gas or slurry process or a combination thereof, most preferably a gas or slurry phase process.

In an embodiment, this invention is directed toward the slurry or gas phase polymerization or copolymerization reactions involving the polymerization of one or more monomers having from 2 to 30 carbon atoms, preferably 2–12 carbon atoms, and more preferably 2 to 8 carbon atoms. The invention is particularly well suited to the copolymerization reactions involving the polymerization of one or more olefin monomers of ethylene, propylene, butene-1, pentene-1, 4-methyl-pentene-1, hexene-1, octene-1, -decene-1, 3-methyl-pentene-1, 3,5,5-trimethyl-hexene-1 and cyclic olefins or a combination thereof. Other monomers can include vinyl monomers, diolefins such as dienes, polyenes, norbornene, norbomadiene monomers. Preferably a copolymer of ethylene is produced, where the comonomer is at least one alpha-olefin having from 4 to 15 carbon atoms, preferably from 4 to 12 carbon atoms, more preferably from 4 to 8 carbon atoms and most preferably from 4 to 7 carbon atoms. In an alternate embodiment, the geminally disubstituted olefins disclosed in WO 98/37109 may be polymerized or copolymerized using the invention herein described.

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In a particularly preferred embodiment the process of the invention relates to the polymerization of ethylene and at least one comonomer having from 4 to 8 carbon atoms, preferably 4 to 7 carbon atoms. Particularly, the comonomers are butene-l, 4-methyl-pentene-1, hexene-1 and octene-1, the most preferred being hexene-1 and/or butene-1.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably in the range of from about 100 psig (690 kPa) to about 400 psig (2759 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C.

The productivity of the catalyst or catalyst system is influenced by the main monomer partial pressure. The preferred mole percent of the main monomer, ethylene or propylene, preferably ethylene, is from about 25 to 90 mole percent and the monomer partial pressure is in the range of from about 75 psia (517 kPa) to about 300 psia (2069 kPa), which are typical conditions in a gas phase polymerization process.

In a preferred embodiment, the reactor utilized in the present invention and the process of the invention produce greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 185° F. (85° C.) to about 230° F. (110° C.). Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst as a slurry in isobutane or as a dry free flowing powder is injected regularly to the reactor loop, which is itself filled with circulating slurry of growing polymer particles in a diluent of isobutane containing monomer and comonomer. Hydrogen, optionally, may be added as a molecular weight control. The reactor is maintained at pressure of about 525 psig to 625 psig (3620 kPa to 4309 kPa) and at a temperature in the range of about 140° F. to about 220° F. (about 60° C. to about 104° C.) depending on the desired polymer density. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of ethylene in the reactor liquid medium is in the range of from about 1 to 10 weight percent, preferably from about 2 to about 7 weight percent, more preferably from about 2.5 to about 6 weight percent, most preferably from about 3 to about 6 weight percent. A preferred process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. No. 5,712,352, which are herein fully incorporated by reference.

In another preferred embodiment the one or all of the catalysts are combined with up to 10 weight % of a metal stearate, (preferably a aluminum stearate, more preferably aluminum distearate) based upon the weight of the catalyst, any support and the stearate, preferably 2 to 3 weight %. In an alternate embodiment a solution of the metal stearate is fed into the reactor. In another embodiment the metal stearate is mixed with the catalyst and fed into the reactor separately. These agents may be mixed with the catalyst or may be fed into the reactor in a solution with or without the catalyst system or its components.

The catalyst and/or the activator may be placed on, deposited on, contacted with, incorporated within, adsorbded, or absorbed in a support. Typically the support can be of any of the solid, porous supports, including microporous supports. Typical support materials include talc; inorganic oxides such as silica, magnesium chloride, alumina, silica-alumina; polymeric supports such as polyethylene, polypropylene, polystyrene, cross-linked polystyrene; and the like. Preferably the support is used in finely divided form. Prior to use the support is preferably partially or completely dehydrated. The dehydration may be done physically by calcining or by chemically converting all or part of the active hydroxyls. For more information on how to support catalysts please see U.S. Pat. No. 4,808,561 which discloses how to support a metallocene catalyst system. The techniques used therein are generally applicable for this invention.

In a preferred embodiment, the polyolefin recovered typically has a melt index as measured by ASTM D-1238, Condition E, at 190° C. of 3000 g/10 min or less. In a preferred embodiment the polyolefin is ethylene homopolymer or copolymer. IN a preferred embodiment for certain applications, such as films, molded article and the like a melt index of 100 g/10 min or less is preferred. For some films and molded article a melt index of 10 g/10 min is preferred. In a preferred embodiment the polymer produced has a molecular weight of 200,000 Daltons or more.

In a preferred embodiment the catalyst system described above is used to make a polyethylene having a density of between 0.88 and 0.970 g/cm$^3$ (as measured by ASTM 2839), a melt index of 1.0 or less g/10 min or less (as measured by ASTM D-1238, Condition E, at 190° C.). Polyethylene having a melt index of between 0.01 to 10 dg/min is preferably produced. In some embodiments, a density of 0.915 to 0.940g/cm$^3$ would be preferred, in other embodiments densities of 0.930 to 0.960g/cm$^3$ are preferred.

The polyolefins then can be made into films, molded articles, sheets, wire and able coating and the like. The films may be formed by any of the conventional technique known in the art including extrusion, co-extrusion, lamination, blowing and casting. The film may be obtained by the flat film or tubular process which may be followed by orientation in an uniaxial direction or in two mutually perpendicular directions in the plane of the film to the same or different extents. Orientation may be to the same extent in both directions or may be to different extents. Particularly preferred methods to form the polymers into films include extrusion or coextrusion on a blown or cast film line.

The films produced may further contain additives such as slip, antiblock, antioxidants, pigments, fillers, antifog, UV stabilizers, antistats, polymer processing aids, neutralizers, lubricants, surfactants, pigments, dyes and nucleating agents. Preferred additives include silicon dioxide, synthetic silica, titanium dioxide, polydimethylsiloxane, calcium carbonate, metal stearates, calcium stearate, zinc stearate, talc, BaSO$_4$, diatomaceous earth, wax, carbon black, flame retarding additives, low molecular weight resins, hydrocarbon resins, glass beads and the like. The additives may be present in the typically effective amounts well known in the art, such as 0.001 weight % to 10 weight %.

This invention further relates to a library of a plurality of metal compounds represented by the formula above. These libraries may then be used for the simultaneous parallel screening of catalysts by combining the library with one or more olefins, preferably in order to determine the relative capabilities of the different compounds.

EXAMPLES

Mn and Mw were measured by gel permeation chromatography on a waters 150° C. GPC instrument equipped with differential refraction index detectors. The GPC columns were calibrated by running a series of narrow polystyrene standards and the molecular weights were calculated using Mark Houwink coefficients for the polymer is question.
Density was measured according to ASTM D 1505,
Melt Index (MI) I$_2$ and I$_{21}$ were measured according to ASTM D-1238, Condition E, at 190° C.
Melt Index Ratio (MIR) is the ratio of I$_{21}$ over I$_2$ as determined by ASTM D-1238.
Weight % comonomer was measured by proton NMR.
MWD=Mw/Mn

Example 1

Catalyst A Preparation

Preparation of [iPrNH(o-C$_6$H$_4$)]$_2$O

A 250 mL one-neck flask was charged with [H$_2$N(o-C$_6$H$_4$)]$_2$O (10.0 g, 50 mmol), acetone (15 mL), activated Zn dust (25.0 g, 382 mmol) and glacial acetic acid (100 mL). The flask was capped with a rubber septum, connected to an oil-bubbler via a needle and then heated under rapid stirring to 60° C. for 24 h. After cooling to room temperature the reaction mixture was poured onto ice (200 mL), concentrated aqueous NH$_3$ (200 mL), and methylene chloride (150 mL). The layers were separated and the aqueous layer extracted with methylene chloride (2×100 mL). The combined methylene chloride layers were dried over MgSO$_4$. Removal of methylene chloride in vacuo afforded crude material as an orange oil. The oil was dissolved in acetone (150 mL) and concentrated HCl (10 mL) was added. Within one minute colorless crystals began to form. The mixture was allowed to stand overnight and the colorless crystalline solid was isolated by filtration, washed with acetone, and dried overnight under vacuum. A mixture of aqueous NaOH (100 mL, 10%) and ether (100 mL) was added to this solid. The mixture was stirred until the solid dissolved. The layers were separated and the aqueous layer extracted with ether (3×50 mL). The combined organic layers were dried over MgSO$_4$. Activated charcoal was added prior to filtering through a bed of Celite. Ether was removed in vacuo leaving a pale yellow oil (yield: 13.2 g, 93%). $^1$H NMR (C$_6$D$_6$) δ 6.98(t, 2), 6.63 (d, 2), 6.55 (t, 2), 4.14 (br s, 2), 3.37 (br m, 2), 0.89 (d, 12). $^{13}$C NMR (C$_6$D$_6$) δ 144.8, 140.0, 125.1, 118.8, 117.1, 112.5, 44.4, 23.2.

Preparation of {[iPrN(o-C$_6$H$_4$)]$_2$O}ZrCl$_2$·C$_7$H$_8$

[iPrNH(o-C$_6$H$_4$)]$_2$O (3.02 g, 10.6 mmol) and Zr(NMe$_2$)$_4$ (2.84 g, 10.6 mmol) were dissolved in pentane (40 mL). The solution was stirred at room temperature for 3 h. All volatile components were removed in vacuo to give an oil. To this oil was added toluene (40 mL) and Me$_3$SiCl (2.9 g, 26.7 mmol). The solution quickly turned bright orange and was left to stand at room temperature for 14 h. Small amounts of solid were removed by filtration and pentane (40 mL) added. The solution was cooled to −25° C. for 24 h. A solid was isolated by filtration (4.11 g, 72%). According to $^1$H NMR spectroscopy one equivalent of toluene was present. $^1$H NMR (CD$_2$Cl$_2$, resonances for toluene are not given) δ 7.67 (d, 2), 7.08 (t, 2), 6.83 (d, 2), 6.77 (t, 2), 4.66 (sept, 2), 1.52 (d, 12). $^{13}$C NMR (CD$_2$Cl$_2$, toluene resonances not given) δ 148.2, 143.4, 126.1, 117.7, 114.7, 113.8, 48.9, 20.0. Analysis calculated for C$_{25}$H$_{30}$Cl$_2$N$_2$OZr: C, 55.95; H, 5.63, N, 5.22. Found: C, 55.84; H, 5.61; N, 5.27.

To 1.239 g of MAO (4.131 g of a 30 weight percent solution in toluene, Albemarle) and 4.274 g of toluene in a 250 mL round bottom flask was added 0.037 g of {[iPrN (o-C$_6$H$_3$)]$_2$O}ZrCl$_2$·C$_7$H$_8$. The solution was stirred for 15 minutes. 3.098 g of silica (Davison 948, calcined at 800° C.) was added followed by mixing. The mixture was dried overnight under vacuum yielding 4.114 g of finished catalyst with a loading of 0.14 weight percent zirconium and an Al/Zr ratio of 310:1.

Example 2
Slurry-Phase Ethylene-Hexene Polymerization

Polymerization was performed in the slurry-phase in a 1-liter autoclave reactor equipped with a mechanical stirrer, an external water jacket for temperature control, a septum inlet and vent line, and a regulated supply of dry nitrogen and ethylene. The reactor was dried and degassed at 160° C. Isobutane (400 mL) was added as a diluent, 35 mL of 1-hexene, and 0.4 mL of a 25 weight percent triisobutyl aluminum solution in hexane was added as a scavenger using a gas tight syringe. The reactor was heated to 60° C. 0.256 g of finished catalyst A was added with ethylene pressure and the reactor was pressurized with 79 psi (545 kPa) of ethylene. The polymerization was continued for 30 minutes while maintaining the reactor at 60° C. and 79 psi (545 kPa) by constant ethylene flow. The reaction was stopped by rapid cooling and venting. No polymer was recovered.

Example 3
Catalyst B Preparation

To 1.902 g of MAO (6.340 g of a 30 weight percent solution in toluene, Albemarle) and 6.521 g of toluene in a 250 mL round bottom flask was added 0.126 g of {[(CD$_3$)$_2$MeCN(o-C$_6$H$_3$)]$_2$O}ZrCl$_2$. The solution was stirred for 15 minutes. 5.003 g of silica (Davison 948, calcined at 600° C.) was added followed by mixing. The mixture was dried overnight under vacuum yielding 6.869 g of finished catalyst with a loading of 0.35 weight percent zirconium and an Al/Zr ratio of 123:1. The {[(CD$_3$)$_2$MeCN(o-C$_6$H$_3$)]$_2$O}ZrCl$_2$ was prepared according to the method in Baumann, Journal of the American Chemical Society, Vol 119, pg 3830, 1997.

Example 4
Slurry-Phase Ethylene-Hexene Polymerization

Polymerization was performed in the slurry-phase in a 2-liter autoclave reactor equipped with a mechanical stirrer, an external waterjacket for temperature control, a septum inlet and vent line, and a regulated supply of dry nitrogen and ethylene. The reactor is dried and degassed at 100° C. Hexane (800 mL) is added as a diluent, 90 mL of 1-hexene, and 0.2 mL of a 25 weight percent triethyl aluminum solution in heptane is added as a scavenger using a gas tight syringe. The reactor was heated to 60° C. 0.400 g of finished catalyst B was added with nitrogen pressure and the reactor was pressurized with 75 psi (545 kPa) of ethylene. The polymerization was continued for 30 minutes while maintaining the reactor at 60° C. and 75 psi (517 kPa) by constant ethylene flow. The reaction was stopped by rapid cooling and venting. 8.8 g of ethylene-hexene copolymer were recovered (MW=281,700, MWD=4.68, 5.6 weight percent hexene, activity=229 g PE/mmol cat.·atm·h).

Example 5
Catalyst C Preparation

To 2.034 g of MAO (6.783 g of a 30 weight percent solution in toluene, Albemarle) and 7.216 g of toluene in a 250 mL round bottom flask was added 0.130 g of {[(2,6-Me$_2$C$_6$H$_3$)NCH$_2$CH$_2$]$_2$O}ZrCl$_2$. The solution was stirred for 15 minutes. 5.024 g of silica (Davison 948, calcined at 800° C.) was added followed by mixing. The mixture was dried overnight under vacuum yielding 7.131 g of finished catalyst with a loading of 0.35 weight percent zirconium and an Al/Zr ratio of 127:1. The {[(2,6-Me$_2$C$_6$H$_3$)NCH$_2$CH$_2$]$_2$O}ZrCl$_2$ was synthesized according to the method of Aizenberg, Organometallics, vol. 17, pg 4795, 1998.

Example 6
Slurry-Phase Ethylene-Hexene Polymerization

The polymerization was conducted as per example 4. 0.200 g of finished catalyst C yielded 37.4 g of ethylene-hexene copolymer (MW=259,900, MWD=6.63, 5.6 weight percent hexene, activity=1950 g PE/mmol cat.·atm·h).

Example 7
Catalyst D Preparation
Preparation of [(2,4,6-Me$_3$C$_6$H$_2$)NHCH$_2$CH$_2$]$_2$NH A 2 L one-armed Schlenk flask was charged with a magnetic stir bar, diethylenetriamine (23.450 g, 0.227 mol), mesityl bromide (90.51 g, 0.455 mol), tris(dibenzylideneacetone)dipalladium (1.041 g, 1.14 mmol), racemic-2,2'-bis(diphenylphosphino)-1,1'-binaphthyl (2.123 g, 3.41 mmol), sodium tert-butoxide (65.535 g, 0.682 mol), and toluene (800 mL). The reaction mixture was heated to 95° C. and stirred. After 4 days the reaction was complete, as judged by proton NMR spectroscopy. All solvent was removed under vacuum and the residues dissolved in diethyl ether (1 L). The ether was washed three times with water (1 L) and saturated aqueous NaCl (500 mL) and dried over magnesium sulfate. Removal of the ether in vacuo yielded a red oil which was dried at 70° C. for 12 h under vacuum (yield: 71.10 g, 92%). $^1$H NMR δ 6.83 (s, 4), 3.39 (br s, 2), 2.86 (t, 4), 2.49 (t, 4), 2.27 (s, 12), 2.21 (s, 6), 0.68 (br s, 1). $^{13}$C NMR δ 143.74, 131.35, 129.83, 129.55, 50.17, 48.56, 20.70, 18.51.

Preparation of {[(2,4,6-Me$_3$C$_6$H$_2$)NCH$_2$CH$_2$]$_2$NH}ZrMe$_2$ 10.798 g of [(2,4,6-Me$_3$C$_6$H$_2$)NHCH$_2$CH$_2$]$_2$NH (31.8 mmol) was dissolved in 250 mL of toluene in a 500 mL round bottom flask. 7.411 g of ZrCl$_4$ (31.8 mmol) was added as a solid and the mixture heated to 80° C. with stirring for 24 hours. The mixture was cooled to room temperature (the insoluble product {[(2,4,6-Me$_3$C$_6$H$_2$)NHCH$_2$CH$_2$]$_2$NH}ZrCl$_4$ can be isolated by filtration and stored for future use).and 43.5 mL of MeMgBr (3.0 M in ether, 130.3 mmol) added dropwise with stirring over 30 minutes. The mixture was stirred for 60 minutes followed by filtration to remove MgClBr. The toluene and ether were removed under vacuum and the solids extracted with toluene (200 mL). The volume of toluene was reduced to 10 mL and 250 mL of pentane added causing the precipitation of a pale brown solid. The solid product was isolated by filtration, washed with 50 mL of cold pentane, and dried under vacuum (15.201 g, 86% yield). $^1$H NMR (C$_6$D$_6$, δ) 6.98 (s, 2), 6.96 (s, 2), 3.32 (m, 2), 3.12 (m, 2), 2.54 (s, 6), 2.42 (s, 6), 2.36 (m, 4), 2.21 (s, 6), 1.16 (s, 1), 0.24 (s, 3), 0.07 (s, 3). $^{13}$C NMR (C$_6$D$_6$, δ) 146.56, 136.07, 135.55, 134.23, 130.29, 129.98, 57.46, 51.27, 42.45, 39.63, 21.44, 19.39, 19.28. Analysis calculated for C$_{24}$H$_{37}$N$_3$Zr: C, 62.83; H, 8.13; N, 9.16. Found: C, 62.91; H, 8.02; N, 9.04.

To 0.617 g of MAO (2.058 g of a 30 weight percent solution in toluene, Albemarle) and 3.009 g of toluene in a 250 mL round bottom flask was added 0.080 g of {[(2,4,6-Me$_3$C$_6$H$_2$)NCH$_2$CH$_2$]$_2$NH}ZrMe$_2$. The solution was stirred for 15 minutes. 3.000 g of silica (Davison 948, calcined at 800° C.) was added followed by mixing. The mixture was dried overnight under vacuum yielding 3.528 g of finished catalyst with a loading of 0.43 weight percent zirconium and an Al/Zr ratio of 61:1.

Example 8

Slurry-Phase Ethylene-Hexene Polymerization

Polymerization was performed in the slurry-phase in a 1-liter autoclave reactor equipped with a mechanical stirrer, an external water jacket for temperature control, a septum inlet and vent line, and a regulated supply of dry nitrogen and ethylene. The reactor was dried and degassed at 160° C. Isobutane (400 mL) was added as a diluent, 35 mL of 1-hexene, and 0.7 mL of a 25 weight percent trioctyl aluminum solution in hexane was added as a scavenger using a gas tight syringe. The reactor was heated to 60° C. 0.078 g of finished catalyst D was added with ethylene pressure and the reactor was pressurized with 74 psi (510 kPa) of ethylene. The polymerization was continued for 30 minutes while maintaining the reactor at 60° C. and 74 psi (510 kPa) by constant ethylene flow. The reaction was stopped by rapid cooling and venting. 59.2 g of ethylene-hexene copolymer were recovered (MW=578,900, MWD=5.40, 11.8 weight percent hexene, activity=6530 g PE/mmol cat.·atm·h).

Example 9

Catalyst E Preparation

To 11.230 g of MAO (37.434 g of a 30 weight percent solution in toluene, Albemarle) and 43.002 g of toluene in a 500 mL round bottom flask was added 0.742 g of {[(2,4,6-Me$_3$C$_6$H$_2$)NCH$_2$CH$_2$]$_2$NH}ZrMe$_2$. (Synthesized according to the procedure in Example 7.) The solution was stirred for 15 minutes. 30.002 g of silica (Davison 948, calcined at 600° C.) was added followed by mixing. The mixture was dried overnight under vacuum yielding 41.002 g of finished catalyst with a loading of 0.35 weight percent zirconium and an Al/Zr ratio of 120:1.

Example 10

Gas-Phase Ethylene-Hexene Polymerization

Catalyst E described above was used for ethylene-hexene copolymerization studies described below. A continuous fluid bed gas-phase reactor operated at 300 psi (2.07 MPa) total pressure and 1.64 ft/s (0.5 m/s) cycle gas velocity was used for determining catalyst efficiency, ability to incorporate comonomer (1-hexene) and molecular weight capability. The polymer properties were as follows: 8.4 weight percent hexene, MI$_2$= 0.31, MI$_{21}$=13.53, MIR=43.65, density 0.9243 g/cm$^3$. A summary of the process data is included in Table 1.

TABLE 1

| | |
|---|---|
| H$_2$ conc. (ppm) | 6451 |
| C$_2$ conc. (mol %) | 35.0 |
| Hexene conc. (mol %) | 0.40 |
| H$_2$/C$_2$ Ratio | 184.5 |
| C$_6$/C$_2$ Ratio | 0.087 |
| Reactor Temp (F./C.) | 145/62.8 |
| Avg. Bed weight (g) | 1891 |
| Production (g/h) | 315 |
| Residence Time (h) | 6.0 |
| Productivity (g/g) - MB$^1$ | 696 |

TABLE 1-continued

| | |
|---|---|
| Productivity (g/g) - XRF$^2$ | 1171 |
| Total Bed Turnovers | 3.0 |

$^1$MB = Material Balance
$^2$XRF = X-ray Fluoresence

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

What is claimed is:

1. A polymerization process comprising combining in the gas or slurry phase an olefin with an activator, a support and a compound represented by the following formula:

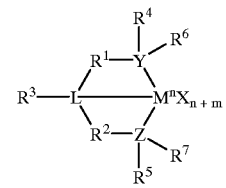

wherein
M is a group 3 to 14 metal,
each X is independently an anionic leaving group,
n is the oxidation state of M,
m is the formal charge of the YZL ligand,
Y is a group 15 element,
Z is a group 15 element,
L is a group 15 or 16 element,
R$^1$ and R$^2$ are independently a C$_1$ to C$_{20}$ hydrocarbon group, a heteroatom containing group, silicon, germanium, tin, lead, or phosphorus,
R$^1$ and R$^2$ may also be interconnected to each other,
R$^3$ is absent, or is hydrogen, a group 14 atom containing group, a halogen, or a heteroatom containing group,
R$^4$ and R$^5$ are independently an aryl group, a substituted aryl group, a cyclic alkyl group, a substituted cyclic alkyl group, or a multiple ring system,
R$^6$ and R$^7$ are independently absent, hydrogen, halogen, a heteroatom, a hydrocarbyl group, or a heteroatom containing group.

2. The process of claim 1 wherein M is a group 4, 5 or 6 transition metal.

3. The process of claim 1 wherein M is zirconium or hafnium.

4. The process of claim 1 wherein each X is independently hydrogen, halogen or a hydrocarbyl group.

5. The process of claim 1 wherein R$^1$ and R$^2$ are independently a C$_1$ to C$_6$ hydrocarbon group.

6. The process of claim 1 wherein R$^1$ and R$^2$ are a C$_1$ to C$_{20}$ alkyl, aryl or aralkyl group.

7. The process of claim 1 wherein m is 0, −1, −2, or −3 and n is +3, +4 or +5.

8. The process of claim 1 wherein R$^3$ is absent, hydrogen or methyl.

9. The process of claim 1 wherein R$^4$ and R$^5$ are independently a hydrocarbon group having up to 20 carbon atoms.

10. The process of claim 1 wherein $R^4$ and $R^5$ are independently an aryl group or an aralkyl group.

11. The process of claim 1 wherein $R^4$ and $R^5$ are independently an aralkyl group.

12. The process of claim 1 wherein $R^4$ and $R^5$ are independently a group represented by the following formula:

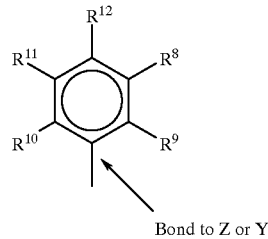

Bond to Z or Y wherein
each $R^8$ to $R^{12}$ are independently hydrogen, or a $C_1$ to $C_{20}$ alkyl group, a heteroatom, or a heteroatom containing group having up to 40 carbon atoms, and any two R groups can combine to form a cyclic group or a heterocyclic group.

13. The process of claim 12 wherein
$R^8$ is methyl, ethyl, propyl or butyl and/or
$R^9$ is methyl, ethyl, propyl or butyl, and/or
$R^{10}$ is methyl, ethyl, propyl or butyl, and/or
$R^{11}$ is methyl, ethyl, propyl or butyl and/or
$R^{12}$ is methyl, ethyl, propyl or butyl.

14. The process of claim 12 wherein $R^9$, $R^{10}$ and $R^{12}$ are methyl and $R^8$ and $R^{11}$ are hydrogen.

15. The process of claim 1 wherein the activator comprises alkyl aluminum compounds, alumoxanes, modified alumoxanes, non-coordinating anions, boranes, borates and/or ionizing compounds.

16. The process of claim 1 wherein the olefin comprises ethylene.

17. The process of claim 1 wherein the olefin comprises propylene.

18. The process of claim 1 wherein the olefin comprises ethylene and a $C_3$ to $C_{20}$ alpha olefin.

19. The process of claim 1, wherein the olefin comprises ethylene and hexene and/or butene.

20. The process of claim 1, wherein the polymer produced has a molecular weight of 200,000 Daltons or more.

21. The process of claim 1 wherein the transition metal compound and/or the activator are placed on a support before being placed in the gas or slurry phase.

22. The process of claim 21 wherein the support is a finely divided polyolefin, talc, or an oxide of silica, magnesia, titania, alumina, or silica-alumina.

23. The process of claim 1 wherein the transition metal compound and the activator are combined, then placed on a support, then placed in the gas or slurry phase.

24. The process of claim 1 wherein a metal stearate is combined with the transition metal compound and/or the activator and/or a support.

25. The process of claim 24 wherein the metal stearate is an aluminum stearate.

26. The process of claim 25 wherein the aluminum stearate is aluminum distearate.

27. The process of claim 1 wherein the polymerization occurs in a gas phase at a reactor temperature of 30° to 120° C.

28. The process of claim 1 wherein the polymerization occurs in the gas phase at a reactor temperature of 60° to 115° C.

29. The process of claim 28 wherein the temperature is 70° to 110° C.

30. The process of claim 1 wherein the polymerization occurs in the slurry phase as particle form polymerization at a temperature of 85° C. to 110° C.

31. The process of claim 1 wherein the polymerization occurs in the slurry phase in a loop reactor at a temperature of 60° to 104° C.

32. A polymerization process comprising combining in the gas or slurry phase an olefin with an activator, a support and a compound represented by the following formula:

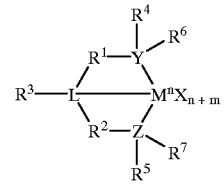

wherein
M is a group 3 to 14 metal,
each X is independently an anionic leaving group,
n is the oxidation state of M,
m is the formal charge of the YZL ligand,
Y is a group 15 element,
Z is a group 15 element,
L is a group 15 or 16 element,
$R^1$ and $R^2$ are independently a $C_1$ to $C_{20}$ hydrocarbon group, a heteroatom containing group, silicon, germanium, tin, lead, or phosphorus,
$R^1$ and $R^2$ may also be interconnected to each other,
$R^3$ is absent, hydrogen, a group 14 atom containing group, a halogen, or a heteroatom containing group,
$R^4$ and $R^5$ are independently an aryl group, a substituted aryl group, a cyclic alkyl group, a substituted cyclic alkyl group, or a multiple ring system,
$R^6$ and $R^7$ are independently absent, hydrogen, halogen, a heteroatom, a hydrocarbyl group, or a heteroatom containing group, provided however that L is bound to one of Y or Z and one of $R^1$ or $R^2$ is bound to L and not to Y or Z.

33. A process to produce a film comprising extruding, blowing or casting a film from polymer produced by a polymerization process comprising combining an olefin in the gas or slurry phase with an activator, a support and a compound represented by the following formula:

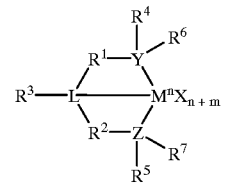

wherein
M is a group 3 to 14 metal,
each X is independently an anionic leaving group,
n is the oxidation state of M, m is the formal charge of the YZL ligand, Y is a group 15 element, Z is a group 15 element, L is a group 15 or 16 element, $R^1$ and $R^2$ are independently a $C_1$ to $C_{20}$ hydrocarbon group, a heteroatom containing group, silicon, germanium, tin, lead, or phosphorus, $R^1$ and $R^2$ may also be interconnected to each other, $R^3$ is absent, hydrogen, a group 14 atom containing group, a halogen, or a heteroatom containing group, $R^4$ and $R^5$ are independently an aryl group, a substituted aryl group, a cyclic alkyl group, a substituted cyclic alkyl group, or a multiple ring system, $R^6$ and $R^7$ are independently absent, hydrogen, halogen, a heteroatom a hydrocarbyl group, or a heteroatom containing group.

34. The process of claim 33 wherein the film is a blown film.

35. A polymerization process comprising combining in the gas or slurry phase an olefin with an activator, a support and a compound represented by the following formula:

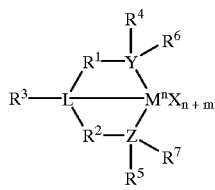

wherein

M is a group 3 to 14 metal, each X is independently an anionic leaving group, n is the oxidation state of M, m is the formal charge of the YZL ligand, Y is a group 15 element, Z is a group 15 element, L is a group 15 element, $R^1$ and $R^2$ are independently a $C_1$ to $C_{20}$ hydrocarbon group, a heteroatom containing group, silicon, germanium, tin, lead, or phosphorus, $R^1$ and $R^2$ may also be interconnected to each other, $R^3$ is absent, or is hydrogen, a halogen, or a heteroatom containing group, $R^4$ and $R^5$ are independently an aryl group, a substituted aryl group, a cyclic alkyl group, a substituted cyclic alkyl group, or a multiple ring system, $R^6$ and $R^7$ are independently absent or hydrogen, halogen, a heteroatom or a hydrocarbyl group, or a heteroatom containing group.

36. A polymerization process comprising combining in the gas or slurry phase an olefin with an activator, a support and a compound represented by the following formula:

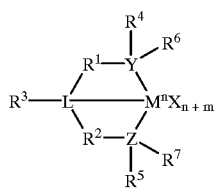

wherein

M is a group 3 to 14 metal, each X is independently an anionic leaving group, n is the oxidation state of M, m is the formal charge of the YZL ligand, Y is a group 15 element, Z is a group 15 element, L is a group 15 element, $R^1$ and $R^2$ are independently a linear $C_1$ to $C_{20}$ hydrocarbon group, a heteroatom containing group, silicon, germanium, tin, lead, or phosphorus, $R^1$ and $R^2$ may also be interconnected to each other, $R^3$ is absent, or is hydrogen, a halogen, or a heteroatom containing group, $R^4$ and $R^5$ are independently an aryl group, a substituted aryl group, a cyclic alkyl group, a substituted cyclic alkyl group, or a multiple ring system, $R^6$ and $R^7$ are absent.

37. A polymerization process comprising combining in the gas or slurry phase an olefin with an activator, a support and a compound represented by the following formula:

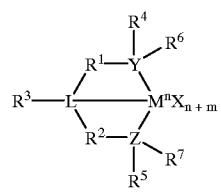

wherein

M is a group 3 to 12 transition metal, each X is independently an anionic leaving group, n is the oxidation state of M, m is the formal charge of the YZL ligand, Y is a group 15 element, Z is a group 15 element, L is a group 15 element, $R^1$ and $R^2$ are independently a $C_1$ to $C_{20}$ hydrocarbon group, a heteroatom containing group, silicon, germanium, tin, lead, or phosphorus, $R^1$ and $R^2$ may also be interconnected to each other, $R^3$ is absent, or is hydrogen, a halogen, or a heteroatom containing group, $R^4$ and $R^5$ are independently a group represented by the following formula:

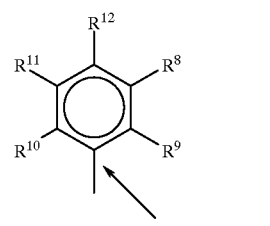

Bond to Z or Y wherein $R^9$, $R^{10}$ and $R^{12}$ are independently a methyl, ethyl, propyl or butyl group and $R^8$ and $R^{11}$ are hydrogen; and $R^6$ and $R^7$ are absent.

38. A polymerization process comprising combining in the gas or slurry phase an olefin with an activator, a support and a compound represented by the following formula:

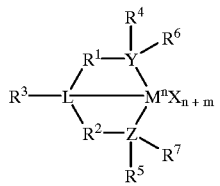

wherein
M is a group 3 to 14 metal,
each X is independently an anionic leaving group,
n is the oxidation state of M,
m is the formal charge of the YZL ligand,
Y is a group 15 element,
Z is a group 15 element,
L is a group 15 element,
$R^1$ and $R^2$ are independently a linear $C_1$ to $C_{20}$ hydrocarbon group, a heteroatom containing group, silicon, germanium, tin, lead, or phosphorus,
$R^1$ and $R^2$ may also be interconnected to each other,
$R^3$ is hydrogen, or a halogen,
$R^4$ and $R^5$ are independently an aryl group, a substituted aryl group, a cyclic alkyl group, a substituted cyclic alkyl group, or a multiple ring system,
$R^6$ and $R^7$ are absent.

* * * * *

UNITED STATES PATENT AND TRADEMARK OFFICE
CERTIFICATE OF CORRECTION

PATENT NO. : 6,271,325 B1  
DATED : August 7, 2001  
INVENTOR(S) : David H. McConville and Richard R. Schrock It is certified that error appears in the above-identified patent and that said Letters Patent is hereby corrected as shown below:

<u>Title page,</u>  
Item [73], Assignee, please insert -- Massachusetts Institute of Technology, Boston, Massachusetts --, after "Univation Technologies, LLC, Houston, Texas (US)" to show co-ownership.

Signed and Sealed this

First Day of October, 2002

*Attest:*

JAMES E. ROGAN  
*Attesting Officer*     Director of the United States Patent and Trademark Office